US009545619B2

United States Patent
Wang et al.

(10) Patent No.: US 9,545,619 B2
(45) Date of Patent: Jan. 17, 2017

(54) CATALYST MATERIALS FOR HYDROGENATING OLEFINS AND SHIFTING CARBON MONOXIDE

(71) Applicant: CLARIANT CORPORATION, Louisville, KY (US)

(72) Inventors: Justin X. Wang, Louisville, KY (US); Jason E. Spencer, Palmyra, IN (US); Jennifer G. Renn, Sellersburg, IN (US); Yeping Cai, Louisville, KY (US)

(73) Assignee: Clariant Corporation, Louisville, KY (US)

( * ) Notice: Subject to any disclaimer, the term of this patent is extended or adjusted under 35 U.S.C. 154(b) by 0 days.

(21) Appl. No.: 14/560,057

(22) Filed: Dec. 4, 2014

(65) Prior Publication Data

US 2016/0158732 A1 Jun. 9, 2016

(51) Int. Cl.
| | |
|---|---|
| *C01B 31/20* | (2006.01) |
| *C07C 7/163* | (2006.01) |
| *B01J 21/00* | (2006.01) |
| *B01J 23/06* | (2006.01) |
| *B01J 23/10* | (2006.01) |

(Continued)

(52) U.S. Cl.
CPC ............. *B01J 23/72* (2013.01); *B01J 23/755* (2013.01); *B01J 23/80* (2013.01); *B01J 23/83* (2013.01); *B01J 23/8892* (2013.01); *B01J 37/0009* (2013.01); *B01J 37/033* (2013.01); *B01J 37/036* (2013.01); *B01J 37/18* (2013.01); *C01B 3/16* (2013.01); *C01B 31/20* (2013.01); *C07C 5/03* (2013.01); *C07C 2521/04* (2013.01); *C07C 2521/06* (2013.01); *C07C 2521/08* (2013.01); *C07C 2521/16* (2013.01); *C07C 2523/72* (2013.01); *C07C 2523/76* (2013.01); *C07C 2523/80* (2013.01); *C07C 2523/83* (2013.01); *C07C 2523/889* (2013.01)

(58) Field of Classification Search
CPC ............ B01J 21/04; B01J 21/06; B01J 21/10; B01J 21/12; B01J 21/14; B01J 21/16; B01J 23/72; B01J 23/78; B01J 23/80; B01J 23/83; B01J 23/84
USPC ............... 502/244, 245, 304, 324, 331, 343, 345,502/346
See application file for complete search history.

(56) References Cited

U.S. PATENT DOCUMENTS 2,061,470 A  11/1936 Larson
2,426,829 A * 9/1947 Kearby ................... C07C 5/322
502/328

(Continued)

FOREIGN PATENT DOCUMENTS

GB  1281112  7/1972

*Primary Examiner* — Cam N. Nguyen (57) ABSTRACT

The disclosure provides catalyst materials useful for hydrogenating olefins and shifting carbon monoxide and methods for using such catalyst materials. In one aspect, the disclosure provides catalyst materials including (a) copper, present in the range of about 20 weight % to about 80 weight %; (b) one or more stabilizer oxides stable under reducing conditions, each stabilizer oxide being a transition metal oxide or a metalloid oxide, the one or more stabilizer oxides being present in a total amount in the range of about 20 weight % to about 70 weight %; and (c) one or more multiple-valence metals, each multiple-valence metal being present in a positive oxidation state, the one or more multiple-valence metals are present in the range of about 0.1 weight % to about 40 weight %, all on an oxide basis.

24 Claims, 4 Drawing Sheets (51) Int. Cl.
*B01J 23/32* (2006.01)
*B01J 23/70* (2006.01)
*B01J 23/72* (2006.01)
*B01J 23/80* (2006.01)
*B01J 23/83* (2006.01)
*B01J 23/889* (2006.01)
*C07C 5/03* (2006.01)
*B01J 37/03* (2006.01)
*B01J 37/18* (2006.01)
*B01J 23/755* (2006.01)
*B01J 37/00* (2006.01)
*C01B 3/16* (2006.01)

(56) References Cited

U.S. PATENT DOCUMENTS

| | | | | |
|---|---|---|---|---|
| 3,448,058 | A * | 6/1969 | Arnold | B01J 23/78 502/174 |
| 4,440,668 | A * | 4/1984 | Chang | B01J 23/002 502/331 |
| 4,562,174 | A * | 12/1985 | Stiles | B01J 23/80 502/174 |
| 4,788,175 | A | 11/1988 | Short | |
| 4,968,660 | A * | 11/1990 | Tijburg | B01J 21/06 502/302 |
| 5,155,086 | A * | 10/1992 | Thakur | B01J 23/80 502/342 |
| 5,387,408 | A * | 2/1995 | Schneider | B01J 23/72 423/656 |
| 5,453,412 | A | 9/1995 | Deckers | |
| 5,928,985 | A * | 7/1999 | Williams | B01J 23/72 502/342 |
| 5,990,040 | A * | 11/1999 | Hu | C01B 3/16 423/437.2 |
| 6,627,572 | B1 * | 9/2003 | Cai | B01J 23/80 502/307 |
| 6,693,057 | B1 * | 2/2004 | Cai | B01J 23/80 502/342 |
| 6,977,317 | B1 | 12/2005 | Frey | |
| 7,435,285 | B2 * | 10/2008 | Junicke | B01D 53/02 502/345 |
| 7,812,060 | B2 | 10/2010 | Gimpel | |
| 8,236,264 | B2 * | 8/2012 | Hatscher | B01D 53/864 423/247 |
| 8,399,718 | B2 | 3/2013 | Wang | |
| 8,623,782 | B2 | 1/2014 | Murakami | |
| 8,680,350 | B2 * | 3/2014 | Hatscher | B01J 23/80 502/340 |
| 8,765,019 | B2 | 7/2014 | Aasberg-Petersen | |
| 2002/0131915 | A1 * | 9/2002 | Shore | B01J 23/56 422/177 |
| 2002/0141938 | A1 * | 10/2002 | Ruettinger | B01J 23/56 423/652 |
| 2002/0147103 | A1 * | 10/2002 | Ruettinger | B01J 23/56 502/66 |
| 2011/0280782 | A1 * | 11/2011 | Hatscher | B01D 53/02 423/247 |
| 2014/0221193 | A1 | 8/2014 | Lee | |
| 2015/0353837 | A1 | 12/2015 | Fleys | |

* cited by examiner

CATALYST MATERIALS FOR HYDROGENATING OLEFINS AND SHIFTING CARBON MONOXIDE

BACKGROUND OF THE INVENTION

Field of the Invention

The disclosure provides catalyst materials useful for hydrogenating olefins and shifting carbon monoxide and methods for using such catalyst materials.

Description of Related Art

Many industrial processes, such as Fischer-Tropsch process, produce an off-gas (or tail gas) that contains hydrogen ($H_2$), carbon monoxide (CO) and hydrocarbons (such as olefins), among other components. While some of the off-gas can be recirculated to the reactor, recirculation of all of the off-gas to the Fischer-Tropsch reactor causes $CO_2$, $CH_4$, and inerts to build up thus reducing the amount of hydrocarbons produced by the Fischer-Tropsch reactor. It can be desirable to use the off-gas stream to form commercially useful products, such as hydrogen. But the presence of olefins and CO in the off-gas stream can hinder its use in further reactions. As a result, olefins and CO are often removed from the off-gas stream. For example, olefins can be hydrogenated to paraffin and CO can be shifted to $H_2$ and $CO_2$.

Typically, olefins in the off-gas are hydrogenated over a Cu or Ni catalyst. The hydrogenation is typically followed by a shift reaction to convert CO and water to $CO_2$ and $H_2$ over a Cu- or Fe-based catalyst. These two steps typically require different catalysts. Or in cases where the same catalyst is used for both steps, the operating reaction conditions for the two reactions significantly different, such that they need to be performed in separate processes.

SUMMARY OF THE INVENTION

There remains a need for a catalyst capable of catalyzing both hydrogenation and the shift reaction, without the need to significantly alter the reaction conditions between two processes. It is particularly important to improve the catalysts employed commercially. In certain aspects, the present invention provides bi-functional catalysts that both hydrogenate olefins and shift CO with high selectivity and high catalytic activity. In certain aspects, the catalysts of the disclosure can simultaneously catalyze hydrogenation and shift reaction processes (e.g., in a single reactor), or two processes can be performed in separate reactors. In certain aspects, the processes of the disclosure can advantageously decrease the operating and capital costs while maintaining or improving conversion yields and/or selectivity. For example, in various aspects the catalysts of the disclosure are highly stable and insensitive to changes in temperature, steam/gas ratio, and space velocity. In addition, substantially no methane or methanol is formed when using the catalysts according to certain aspects of the disclosure, which can be particularly beneficial in commercial applications as these two reactions are highly exothermic and may result in damage to the catalysts and increases in costs.

In one aspect, the present invention provides a catalyst material comprising:
(a) copper, present in the range of about 20 weight % to about 80 weight based on the total weight of the catalyst material, calculated as CuO;
(b) one or more stabilizer oxides, each stabilizer oxide being a transition metal oxide or a metalloid oxide, each stabilizer oxide being stable under reducing conditions, the one or more stabilizer oxides being present in a total amount in the range of about 20 weight % to about 70 weight % based on the total weight of the catalyst material, calculated as the most stable oxide for each metal; and
(c) one or more multiple-valence metals, each multiple-valence metal being present in a positive oxidation state, the one or more multiple-valence metals are present in the range of about 0.1 weight % to about 40 weight % based on the total weight of the catalyst material, calculated as the most stable oxide for each metal.

In another aspect, the present invention provides a method for converting carbon monoxide to carbon dioxide, the method comprising reacting carbon monoxide with water in contact with a catalyst material of the disclosure.

In another aspect, the present invention provides a method for converting olefins to hydrocarbons, the method comprising reacting an olefin with hydrogen in contact with a catalyst material of the disclosure.

In another aspect, the present invention provides a method for simultaneously converting carbon monoxide to carbon dioxide and olefins to hydrocarbons, the method comprising reacting carbon monoxide with water, and one or more olefins with hydrogen in contact with a catalyst material of the disclosure.

DETAILED DESCRIPTION OF THE INVENTION

Before the disclosed methods and materials are described, it is to be understood that the aspects described herein are not limited to specific embodiments, apparati, or configurations, and as such can, of course, vary. It is also to be understood that the terminology used herein is for the purpose of describing particular aspects only and, unless specifically defined herein, is not intended to be limiting.

Throughout this specification, unless the context requires otherwise, the word "comprise" and "include" and variations (e.g., "comprises," "comprising," "includes," "including") will be understood to imply the inclusion of a stated component, feature, element, or step or group of components, features, elements or steps but not the exclusion of any other integer or step or group of integers or steps.

As used in the specification and the appended claims, the singular forms "a," "an" and "the" include plural referents unless the context clearly dictates otherwise.

Ranges can be expressed herein as from "about" one particular value, and/or to "about" another particular value.

When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the term "contacting" includes the physical contact of at least one substance to another substance.

All percentages, ratios and proportions herein are by weight, unless otherwise specified. A weight percent (weight %, also as wt %) of a component, unless specifically stated to the contrary, is based on the total weight of the formulation or composition in which the component is included (e.g., on the total amount of the catalyst material). All mol % values are based on the moles of metal atoms.

In view of the present disclosure, the methods and active materials described herein can be configured by the person of ordinary skill in the art to meet the desired need. In general, the disclosed materials, methods, and apparati provide improvements in catalyst materials utilized in the hydrogenation and shift of off-gas, particularly in the Fischer-Tropsch process. For example, in certain aspects, the catalysts of the disclosure are highly active and selective. In other aspects, the catalysts of the disclosure can simultaneously catalyze hydrogenation and shift reaction processes (e.g., in a single reactor), or two processes can be performed in separate reactors. In certain aspects, the catalysts of the disclosure are highly stable and insensitive to changes in temperature, steam/gas ratio, and space velocity.

One aspect of the disclosure is a catalyst material. The catalyst material can be useful, for example, as a catalyst for use in both hydrogenation and shift reactions, as described in more detail below. The catalyst material includes copper. Copper is present in the range of about 20 weight % to about 80 weight %, based on the total weight of the catalyst material. While the copper can be present in any oxidation state, the amount of copper present is calculated as CuO. The catalyst material also includes one or more stabilizer oxides, each being a transition metal oxide or a metalloid oxide, present in a total amount in the range of about 20 weight % to about 70 weight % based on the total weight of the catalyst material, calculated as the most stable oxide for each metal. Notably, each stabilizer oxide is stable under reducing conditions, as described in more detail below. The catalyst material also includes one or more multiple-valence metals, each multiple-valence metal being present in a positive oxidation state, the one or more multiple-valence metals are present in the range of about 0.1 weight % to about 40 weight % based on the total weight of the catalyst material, calculated as the most stable oxide for each metal.

As the person of ordinary skill in the art will appreciate, the copper may be present in the catalyst material as metallic copper or in the form of an oxidized copper species, for example, copper oxide. In one embodiment, the copper is present as metallic copper. In another embodiment, the copper is present in the form of copper oxide (e.g., CuO). As the person of ordinary skill will appreciate, during operation of the catalyst material in a catalytic process, the copper can be present in metallic form. But the reduction to copper metal (e.g., from copper oxide) can occur in situ in a reactor.

As described above, the copper is present in a range of about 20 weight % to about 80 weight %, based on the total weight of the catalyst material, calculated as CuO. In certain embodiments, the copper may be present in the range of about 20 weight % to about 60 weight %, or about 20 weight % to about 50 weight %, or about 20 weight % to about 48%, or about 30 weight % to about 80 weight %, or about 40 weight % to about 80 weight %, or about 35 weight % to about 80 weight %, or about 35 weight % to about 75 weight %, or about 35 weight % to about 65 weight %, or about 30 weight % to about 70 weight %, about 30 weight % to about 65 weight %, or about 40 weight % to about 60 weight %, or about 41 weight % to about 59 weight %, or about 42 weight % to about 58 weight %, or about 43 weight % to about 57 weight %, or about 43 weight % to about 55 weight %, or about 43 weight % to about 53 weight %, or about 45 weight % to about 60 weight %, or about 45 weight % to about 57 weight %, or about 45 weight % to about 55 weight %, or about 45 weight % to about 53 weight %, or about 47 weight % to about 57 weight %, or about 47 weight % to about 55 weight %, or about 47 weight % to about 53 weight %, or about 47 weight % to about 50 weight %, or about 45 weight % to about 50 weight %, or about 40 weight % to about 50 weight %, or about 45 weight %, or about 46 weight %, or about 47 weight %, or about 47.5 weight %, or about 48 weight %, or about 49 weight %, or about 50 weight %, based on the total weight of the catalyst material, calculated as CuO. In some embodiments, the copper is present in the range of about 43 weight % to about 52 weight % based on the total weight of the catalyst material, calculated as CuO. In other embodiments, the copper is present in the range of about 45 weight % to about 48 weight % based on the total weight of the catalyst material, calculated as CuO.

As described above, the one or more stabilizer oxides are stable under reaction conditions. As used herein, a stabilizer oxide that is "stable under reducing conditions" is one that experiences less than 5% reduction and substantially no structural change under a reducing test reaction, conducted by exposing the catalyst in a 19 mm inner diameter tubular reactor (10 mL whole catalyst particle loading) first to 3% $H_2$ in $N_2$ gas at 230° C. for one hour, then to a gas mixture comprising 46.8% $CO+H_2$, 24% $CO_2$ and 17.5% $CH_4$, with the balance being nitrogen gas, at a temperature of 275° C., a pressure of 400 psi and a steam/gas ratio of 0.6 for 3 hours.

As the person of ordinary skill in the art will appreciate, the one or more stabilizer oxides can be provided in a variety of forms. For example, in certain embodiments, the one or more stabilizer oxides are transition metal oxides. In other embodiments, the one or more stabilizer oxides are metalloid oxides. Suitable stabilizer oxides may be selected, for example, from the group consisting of zinc oxide, aluminum oxide, zirconium oxide, titanium oxide, silicon dioxide, zinc aluminate, magnesium aluminate, zinc aluminate and silica aluminate, calcium aluminate, clays and zeolites. In certain embodiments, the one or more stabilizer oxides are selected from the group consisting of zinc oxide, aluminum oxide, zirconium oxide, titanium oxide, and silicon dioxide and mixtures thereof. In other embodiments, the one or more stabilizer oxides are zinc oxide, aluminum oxide, zinc aluminate or a mixture thereof. In certain aspects, the stabilizer oxide is provided as zinc oxide. In other embodiments, the stabilizer oxide is aluminum oxide.

As described above, the catalyst material comprises from about 20 weight % to about 70 weight % of the one or more stabilizer oxides, based on the total weight of the catalyst material, calculated as the most stable oxide for each metal. In certain embodiments of the catalyst materials as described herein, the one or more stabilizer oxides are present in the range of about 20 weight % to about 60 weight %, or about 20 weight % to about 50 weight %, or about 30 weight % to about 50 weight %, or about 30 weight % to about 70 weight %, or about 40 weight % to about 70 weight %, or about 25 weight % to about 65 weight %, or about 30 weight % to about 65 weight %, or about 30 weight % to about 60 weight %, about 40 weight % to about 60 weight %, or about 41 weight % to about 59 weight %, or about 42 weight % to about 58 weight %, or about 43 weight % to about 57 weight %, or about 43 weight % to about 55 weight %, or about 43 weight % to about 53 weight %, or about 45 weight % to about 60 weight %, or about 45 weight % to about 57 weight %, or about 45 weight % to about 55 weight %, or about 45 weight % to about 53 weight %, or about 47 weight % to about 57 weight %, or about 47 weight % to about 55 weight %, or about 47 weight % to about 53 weight %, or about 47 weight % to about 50 weight %, or about 45 weight % to about 50 weight %, or about 40 weight % to about 50 weight %, or about 30 weight %, or about 40 weight %, or about 45 weight %, or about 46 weight %, or about 47 weight %, or about 47.5 weight %, or about 48 weight %, or about 49 weight %, or about 50 weight %, based on the total weight of the catalyst material, calculated as the most stable oxide for each metal. In some embodiments, the one or more stabilizer oxides are present in the range of about 30 weight % to about 50 weight % based on the total weight of the catalyst material, calculated as the most stable oxide for each metal. In some embodiments, the one or more stabilizer oxides are present in the range of about 43 weight % to about 52 weight % based on the total weight of the catalyst material, calculated as the most stable oxide for each metal. In other embodiments, the one or more stabilizer oxides are present in the range of about 45 weight % to about 48 weight % based on the total weight of the catalyst material, calculated as the most stable oxide for each metal.

The ratio of the copper to the one or more stabilizer oxides can be important for the performance of the catalyst material. Thus, in certain embodiments of the catalyst materials as described herein, the ratio (i.e., by weight, calculated as oxides as described above) of the copper to the one or more stabilizer oxides is in the range of about 3:1 to about 1:2. In various embodiments, the ratio of the copper to the one or more stabilizer oxides is in the range of about 2.5:1 to about 1:1.75, or about 2:1 to about 1.5, or about 1.3:1 to about 1.3:1, or about 2:1 to about 1:1.5, or about 3:1 to about 1:1.25, or about 3:1 to about 1:1, or about 2:1 to about 1:1.25, or about 2:1 to about 1:1, or about 1.5:1 to about 1:2, or about 1:1 to about 2:1, or about 1.5:1 to about 1:1.5, or about 1.5:1 to about 1:1.3, or about 1.5:1 to about 1:1.2, or about 1.5:1 to about 1:1, or about 1.25:1 to about 1:1.25, or about 1.25:1 to about 1:1, or about 1.2:1 to about 1:1.2, or about 1.2:1 to about 1:1, or about 1.1:1 to about 1:1.1, or about 1.1:1 to about 1:1, or about 1.05:1 to about 1:1.05, or about 1.05:1 to about 1:1, or about 1.5:1, or about 1.4:1, or about 1.3:1, or about 1.2:1, or about 1.1:1, or about 1.05:1, or about 1.02:1, or about 1:1. In one particular embodiment, the ratio of the copper to the one or more stabilizer oxides is in the range of about 2:1 to about 1:1. In certain embodiments, the ratio of the copper to the one or more stabilizer oxides is about 1:1.

As described above, the composition includes one or more multiple-valence metals, each present in a positive oxidation state. As used herein, a multiple-valence metal is one that has at least two positive oxidation states between which the metal can be reversibly oxidized and reduced. The higher oxidation state can be reduced to the lower oxidation state under reducing conditions, and the lower oxidation state can be oxidized to the higher oxidation state under oxidative conditions. Examples of suitable multiple-valence metals include, for example, manganese, lanthanum, cerium, chromium, vanadium, iron, cobalt, nickel, molybdenum and tungsten. Advantageously, while the multiple-valence metal may be provided at a single oxidation state in a catalyst product, the multiple-valence metal can be reversibly oxidized and reduced under reaction conditions suitable to hydrogenate olefins and shift CO. For example, manganese may be reversibly oxidized and reduced between manganese (II) and manganese (IV); cerium may be reversibly oxidized and reduced between cerium (III) and cerium (IV); chromium may be reversibly oxidized and reduced between chromium (III) and chromium (VI); vanadium may be reversibly oxidized and reduced between vanadium (III) and vanadium (V); iron may be reversibly oxidized and reduced between iron (II) and iron (III); lanthanum may be reversibly oxidized and reduced between lanthanum (II) lanthanum (III); cobalt may be reversibly oxidized and reduced between cobalt (II) oxide and cobalt (III); nickel may be reversibly oxidized and reduced between nickel (II) oxide and nickel (III); molybdenum may be reversibly oxidized and reduced between molybdenum (IV) and molybdenum (VI); and tungsten may be reversibly oxidized and reduced between tungsten (III) tungsten (VI). In certain embodiments, the one or more multiple-valence metals are selected from group consisting of manganese, cerium, chromium, and vanadium. In other embodiments, the one or more multiple-valence metals are selected from group consisting of manganese and cerium. In some other embodiments, the multiple-valence metal is manganese. As the person of ordinary skill in the art will appreciate, the one or more multiple-valence metals can be provided in a variety of forms. For example, in certain embodiments, the one or more multiple-valence metals may be present in the form of one or more oxides.

As described above, the catalyst material includes from about 0.1 weight % to about 40 weight %, of the one or more multiple-valence metals, based on the total weight of the catalyst material, calculated as the most stable oxide for each metal. In various embodiments, the one or more multiple-valence metals are present in the range of about 0.1 weight % to about 25 weight %, or about 0.1 weight % to about 10 weight %, or about 0.1 weight % to about 5 weight %, or about 0.1 weight % to about 2 weight %, or about 0.5 weight % to about 30 weight %, or about 0.5 weight % to about 25 weight %, or about 0.5 weight % to about 20 weight %, or about 0.5 weight % to about 15 weight %, or about 0.5 weight % to about 10 weight %, or about 0.5 weight % to about 5 weight %, or about 0.5 weight % to about 2 weight %, or about 1 weight % to about 25 weight %, or about 1 weight % to about 20 weight %, or about 1 weight % to about 18 weight %, or about 1 weight % to about 15 weight %, or about 1 weight % to about 12 weight %, or about 1 weight % to about 10 weight %, or about 1 weight % to about 7 weight %, or about 1 weight % to about 5 weight %, or about 5 weight % to about 25 weight %, or about 5 weight % to about 25 weight %, or about 5 weight % to about 20 weight %, or about 5 weight % to about 18 weight %, or about 5 weight % to about 15 weight %, or about 5 weight % to about 12 weight %, or about 5 weight % to about 10 weight %, or about 5 weight % to about 7 weight %, based on the total weight of the catalyst material, calculated as the most stable oxide for each metal. In some embodiments, the one or more multiple-valence metals are present in the range of about 1 weight % to about 25 weight % based on the total weight of the catalyst material, calculated as the most stable oxide for each metal. In some embodiments, the one or more multiple-valence metals are present in the range of about 3 weight % to about 12 weight % based on the total weight of the catalyst material, calculated as the most stable oxide for each metal. In other embodiments, the one or more multiple-valence metals are present in the range of about 0.5 weight % to about 11 weight based on the total weight of the catalyst material, calculated as the most stable oxide for each metal.

As noted above, the ratio of components can be important for the performance of the catalyst material. In certain embodiments of the catalyst materials and methods as described herein, the ratio (i.e., by weight, calculated as oxides) of the copper to the one or more stabilizer oxides to the one or more multiple-valence metals is in the range of about 2:1:0.01 to about 1:2:2. In various embodiments, the ratio of the copper to the one or more stabilizer oxides to the one or more multiple-valence metals is in the range of about 2:1:0.1 to about 1:1.5:1, or about 2:1:0.05 to about 1:1:1, or about 1.5:1:0.05 to about 1:1.5:1, or about 1.5:1:0.05 to about 1:1:1, or about 1.25:1:0.0.5 to about 1:1.25:1, or about 1.25:1:0.1 to about 1:1:1, or about 1.2:1:0.1 to about 1:1.2:1, or about 1.2:1:0.1 to about 1:1:0.1, or about 1.1:1:0.1 to about 1:1.1:1, or about 1.1:1:0.1 to about 1:1:1, or about 1.05:1:0.1 to about 1:1.05:1, or about 1.05:1:0.1 to about 1:1:1, or about 1.5:1:0.1, or about 1.4:1:0.1, or about 1.3:1:0.1, or about 1.2:1:0.1, or about 1.1:1:0.1, or about 1.05:1:0.1, or about 1.02:1:0.1, or about 1:1:0.1, or about 1.5:1:0.2, or about 1.4:1:0.2, or about 1.3:1:0.2, or about 1.2:1:0.2 to about 1.4:1:0.2, or about 1.05:1:0.2 to about 1:1:0.2, or about 1.5:1:0.3 to about 1.1:1:0.3, or about 1.05:1:0.3 to about 1:1:0.3, or about 1.5:1:0.5 to about 1:1:0.5, or about 1.3:1:0.5 to about 1:1:0.5, or about 1.1:1:0.5 to about 1:1:0.5. In one particular embodiment, the ratio of the copper to the one or more stabilizer oxides to the one or more multiple-valence metals is in the range of about 2:1:0.01 to about 1:1:1. In certain embodiments, the ratio of the copper to the one or more stabilizer oxides to the one or more multiple-valence metals is about 1:1:0.1 to about 1:1:0.3. In certain embodiments, the ratio of the copper to the one or more stabilizer oxides to the one or more multiple-valence metals is about 1:1:0.1. In certain embodiments, the ratio of the copper to the one or more stabilizer oxides to the one or more multiple-valence metals is about 1:1:0.2.

In other certain embodiments of the catalyst materials and methods as described herein, the ratio (i.e., by weight, calculated as oxides as described above) of the copper to the one or more multiple-valence metals is in the range of about 5:0.01 to about 5:3. In various embodiments, the ratio of the copper to the one or more multiple-valence metals is in the range of about 5:0.01 to about 5:2, or about 5:0.01 to about 5:1, or about 5:0.01 to about 5:0.5, or about 5:0.01 to about 5:0.1, or about 5:0.02 to about 5:2, or about 5:0.02 to about 5:1, or about 5:0.02 to about 5:0.5, or about 5:0.02 to about 5:0.1, or about 5:0.05 to about 5:2, or about 5:0.05 to about 5:1, or about 5:0.05 to about 5:0.5, or about 5:0.05 to about 5:0.1, or about 5:0.1 to about 5:2, or about 5:0.1 to about 5:1, or about 5:0.1 to about 5:0.5, or about 5:0.1 to about 5:1, or 5:0.2 to about 5:2, or about 5:0.2 to about 5:1, or about 5:0.2 to about 5:0.5, or about 5:0.3 to about 5:2, or about 5:0.3 to about 5:1, or about 5:0.3 to about 5:0.5, or about 5:1 to about 5:2, or about 5:0.1, or about 5:0.2, or about 5:0.3, or about 5:0.4, or about 5:0.5, or about 5:1. In certain embodiments, the ratio of the copper to the one or more multiple-valence metals is about 5:0.1 to about 5:1. In certain embodiments, the ratio of the copper to the one or more multiple-valence metals is about 5:1. In certain embodiments, the ratio of the copper the one or more multiple-valence metals is about 5:0.2.

In one exemplary embodiment of the disclosure, the catalyst material comprises (or, even, consists essentially of) (a) copper; (b) one or more stabilizer oxides selected from zinc oxide and aluminum oxide; and (c) one or more multiple-valence metals selected from manganese and cerium, for example, in the amounts described above. In one such embodiment, the copper and the one or more multiple-valence metals are present as oxides.

In one exemplary embodiment of the disclosure, the catalyst material comprises (or, even, consists essentially of) (a) copper present in the range of about 40 weight % to about 55 weight %, calculated as CuO; (b) zinc and/or aluminum oxide present in an amount of about 30 weight % to about 50 weight %, calculated as oxide; and (c) manganese and/or cerium promoter present in the range of about 1 weight % to about 25 weight %, calculated as the most stable oxide for each metal.

In certain embodiments, the catalyst material includes less than about 20%, less than about 10%, less than about 5%, or even less than about 1% of components other than the copper, the stabilizer oxide(s) and the promoter metal(s). In certain embodiments, the catalyst material includes no other catalytically active species other than those listed above.

The catalyst material may be provided in any suitable form. For example, the active material can be formed as spheres, pellets, cylinders (hollow or otherwise), symmetrical or asymmetrical tri-quadrulobes, or other shape/medium, for example, using extrusion or tableting methods.

The catalyst materials described herein can be provided with a variety of different pore volumes, depending, e.g., on the methods used for making them and the desired end use. For example, in certain embodiments, a catalyst material as described herein has a pore volume within the range of about 0.1 to about 1.5 $cm^3/g$, or about 0.2 to about 1.5 $cm^3/g$, or about 0.3 to about 1.5 $cm^3/g$, or about 0.5 to about 0.5 $cm^3/g$, or about 0.2 to about 0.5 $cm^3/g$, or about 0.3 to about 0.5 $cm^3/g$, or about 0.4 to about 0.5 $cm^3/g$, or about 0.1 to about 1 $cm^3/g$, or about 0.2 to about 1 $cm^3/g$, or about 0.3 to about 1 $cm^3/g$, or about 0.5 to about 1 $cm^3/g$. In various embodiments, a catalyst material as described herein has a pore volume of about 0.1 $cm^3/g$, or about 0.2 $cm^3/g$, or about 0.3 $cm^3/g$, or about 0.4 $cm^3/g$, or about 0.5 $cm^3/g$, or about 1 $cm^3/g$, or about 1.5 $cm^3/g$. In particular embodiments, the catalyst material has a pore volume within the range of about 0.3 to about 0.7 $cm^3/g$. In other particular embodiments, the catalyst material has a pore volume within the range of about 0.4 to about 0.6 $cm^3/g$. In other embodiments, the catalyst material has a pore volume within the range of about 0.2 to about 0.5 $cm^3/g$. The person of ordinary skill in the art can, in view of the methods described herein, provide a desired pore volume to a catalyst material.

Similarly, the catalyst materials described herein can be provided with a variety of different surface areas, depending, e.g., on the methods used for making them and the desired end use. The surface areas are measured using the Brunauer-Emmett-Teller (BET) Surface Area method. In certain embodiments, a catalyst material as described herein has a surface area within the range of from about 10 to about 400 $m^2/g$, or about 50 to about 400 $m^2/g$, or about 70 to about 400 $m^2/g$, or about 100 to about 400 $m^2/g$, or about 200 to about 400 $m^2/g$, or about 300 to about 400 $m^2/g$, or about 10 to about 300 $m^2/g$, or about 50 to about 300 $m^2/g$, or about 70 to about 300 $m^2/g$, or about 100 to about 300 $m^2/g$, or about 200 to about 300 $m^2/g$, or about 100 to about 250 $m^2/g$, or about 10 to about 200 $m^2/g$, or about 50 to about 200 $m^2/g$, or about 70 to about 200 $m^2/g$, or about 100 to about 200 $m^2/g$. In one embodiment, a catalyst material as described herein has a surface area of about 20 to about 300 m$^2$/g. In another embodiment, a catalyst material as described herein has a surface area of about 30 to about 200 m$^2$/g. In another embodiment, a catalyst material as described herein has a surface area of about 70 to about 300 m$^2$/g. The person of ordinary skill in the art can, in view of the methods described herein, provide a desired surface area to a catalyst material.

The catalytic material may be prepared by conventional procedures, as would be understood by the person of ordinary skill in the art. For example, in one embodiment, the active material is made by precipitation. Thus, in one embodiment, the active material is made by precipitation of one or more water soluble raw materials with a precipitation agent. Each raw material may be a water soluble metal material such as, but not limited to, a metal nitrate, a metal sulfate, a metal halide, or a metal acetate; certain raw materials may be provided with the metal species in the anion (e.g. molybdate, manganate, chromate, tungstate, vanadate). In certain embodiments, the raw material is copper nitrate, manganese nitrate, or copper amine. The precipitation agent may be, for example, ammonium hydroxide, ammonium carbonate, a metal hydroxide, or a metal carbonate. In certain embodiments, the precipitation agent is $Na_2CO_3$. The person of ordinary skill in the art can select other suitable precipitation agents. Precipitated materials can be formed into desired shapes using extrusion and/or tableting methods, as would be evident to the person of ordinary skill in the art. The person of ordinary skill in the art will also appreciate that such materials can be formed with or without a binder, depending on the particular metals used and the desired active material properties.

The catalyst materials described herein can be useful in performing hydrogenation and shift reactions in industrial applications, especially of the off-gas of a Fischer-Tropsch process. Advantageously, the hydrogenation and shift reactions can be performed in the same process, e.g., at a single set of conditions. Of course, in other embodiments, the hydrogenation and shift reaction can be performed in separate reactors.

Accordingly, one aspect of the invention is a method for converting carbon monoxide to carbon dioxide (i.e., via the water-gas shift reaction), the method comprising reacting carbon monoxide with water in contact with a catalyst material as described herein. Another aspect of the invention is a method for converting olefins to hydrocarbons (i.e., hydrogenating an olefin), the method comprising reacting an olefin with hydrogen in contact with a catalyst material as described herein. The two aspects described above can be performed, for example, individually (e.g., performing one without performing the other) or consecutively (e.g., in different reactors, for example, under different reaction conditions). In other embodiments, the hydrogenation and shift reaction are performed simultaneously (i.e., under the same reaction conditions at the same time). Thus, another aspect of the invention includes a method for simultaneously converting carbon monoxide to carbon dioxide (i.e., via reaction with water) and hydrogenating olefins, the method comprising reacting carbon monoxide with water, and one or more olefins with hydrogen in contact with a catalyst material of the disclosure. The carbon monoxide and olefins (and, optionally, the hydrogen and/or the water) can be provided, for example, by an off-gas of a Fischer Tropsch reaction process. The methods of the disclosure can be performed using conventional apparati and techniques, and the person of ordinary skill in the art will determine appropriate reaction conditions for a particular system.

As the person of ordinary skill in the art will appreciate, it may be desirable or necessary to activate the catalyst material prior to reaction, for example, to substantially put the copper in the form of metallic copper. Activation can also happen during reaction. In one embodiment, the activation is performed by reduction, for example, with hydrogen gas at elevated temperature (e.g., about 180-280° C., or about 230° C.).

The methods described herein can be performed at a variety of pressures and temperatures. For example, in certain embodiments, the reaction temperature can remain in the range of about 180° C. to about 400° C., in the range of about 180° C. to about 300° C., or about 180° C. to about 250° C., or about 250° C. to about 400° C., or about 190° C. to about 300° C., or about 190° C. to about 350° C., or about 190° C. to about 400° C., or about 220° C. to about 400° C., or about 220° C. to about 300° C., or about 180° C. to about 200° C., or about 180° C. to about 210° C., or about 180° C. to about 220° C., or about 250° C. to about 290° C., or about 260° C. to about 280° C., or about 270° C. to about 280° C. In certain embodiments, the reaction is performed at a pressure in the range of about 0.1 MPa to about 10 MPa, or about 0.5 MPa to about 10 MPa, or about 0.1 MPa to about 1.5 MPa, or about 0.1 MPa to about 2 MPa, or about 0.1 MPa to about 3 MPa, or about 0.1 MPa to about 4 MPa, or about 0.1 MPa to about 5 MPa, or about 0.1 MPa to about 8 MPa, or about 0.5 MPa to about 1 MPa, or about 0.5 MPa to about 1.5 MPa, or about 0.5 MPa to about 2 MPa, or about 0.5 MPa to about 3 MPa, or about 0.5 MPa to about 4 MPa, or about 0.5 MPa to about 5 MPa, or about 0.5 MPa to about 8 MPa, or about 1 to about 2 MPa, or about 1 to about 3 MPa, or about 1 to about 4 MPa, or about 1 to about 5 MPa. Of course, the person of ordinary skill in the art will understand that in certain embodiments and applications the temperatures and pressures may differ from those particularly described here.

While Fischer-Tropsch process off-gas can often include water, in many embodiments it may be desirable to add additional water to the reaction in the form of steam. The methods described herein can be performed at a wide variety of steam/gas ratios. For example, in one embodiment of the methods as described herein, the steam/gas ratio is in the range of about 0.1 to about 2.5 (vol/vol). In certain embodiments. of the methods as described herein, the steam/gas ratio is in the range of about 0.1 to about 2, or about 0.1 to about 1.5, or about 0.5 to about 2.5, or about 0.5 to about 2, or about 0.5 to about 1.5, or about 0.5 to about 1.2, or about 0.2 to about 1.8; about 0.2 to about 2.5, or about 0.1 to about 1.8. Of course, the person of ordinary skill in the art will understand that in certain embodiments and applications the steam/gas ratio may differ from the ratios particularly described here.

The processes described herein can be performed at a variety of dry gas space velocity (DGSV). In some embodiments, the dry gas space velocity is in the range of about 500 hr$^{-1}$ to about 15000 hr$^{-1}$. For example, in some embodiments, the dry gas space velocity is in the range of about 500 hr$^{-1}$ to about 10000 hr$^{-1}$, or about 500 hr$^{-1}$ to about 8000 hr$^{-1}$, or about 1000 hr$^{-1}$ to about 15000 hr$^{-1}$, or about 3000 hr$^{-1}$ to about 15000 hr$^{-1}$, or about 1000 hr$^{-1}$ to about 10000 hr$^{-1}$, or about 1000 hr$^{-1}$ to about 8000 hr$^{-1}$, or about 2000 hr$^{-1}$ to about 8000 hr$^{-1}$, about 2000 hr$^{-1}$ to about 7000 hr$^{-1}$, about 2000 hr$^{-1}$ to about 5000 hr$^{-1}$, or about 4000 hr$^{-1}$ to about 8000 hr$^{-1}$, or about 5000 hr$^{-1}$ to about 8000 hr$^{-1}$, or about 4000 hr$^{-1}$ to about 7000 hr$^{-1}$, or about 3000 hr$^{-1}$ to about 8000 hr$^{-1}$, or about 3000 hr$^{-1}$ to about 7000 hr$^{-1}$, or about 3000 hr$^{-1}$ to about 5000 hr$^{-1}$, or about 1000 hr$^{-1}$, or about 2000 hr$^{-1}$, or about 3000 hr$^{-1}$, or about 4000 hr$^{-1}$, or about 5000 hr$^{-1}$, or about 6000 hr$^{-1}$, or about 7000 hr$^{-1}$, or about 8000 hr$^{-1}$, or about 9000 hr$^{-1}$, or about 10000 hr$^{-1}$. Of course, the person of ordinary skill in the art will understand that in certain embodiments and applications, the dry gas space velocity values may differ from those particularly described here.

The person of ordinary skill in the art will appreciate that the feed gas for the reaction can come from a variety of sources. In certain embodiments, the feed gas is an off-gas from a Fischer-Tropsch process. In other embodiments, the feed gas can come from a gasification process, as is well known in the art. The feed gas can come from, for example, the gasification of coal, heavy residues, biomass, waste and other carbon-rich feedstocks.

The person of ordinary skill in the art will appreciate that various hydrocarbons can be converted in the processes of the disclosure. For example, in certain embodiments, the feed gas includes one or more (e.g., one) hydrocarbons selected from $C_2$-$C_7$ olefins. In some embodiments, the feed gas may comprise ethene, propene, 2-methylpropene, 1-butene, 2-butene, 1-pentene, 2-pentene, 1-hexene, and/or 2-hexene. In some embodiments, the hydrocarbon feed gas comprises ethene and/or propene. In other embodiments, the hydrocarbon feed gas comprises ethene. The olefin content (e.g., one or more olefins) in the feed gas may be present, for example, in an amount in the range of up to about 10%, e.g., about 100 ppm to about 10%, or about 100 ppm to about 7%, or about 100 ppm to about 5%, or less than about 7%, or less than about 5%.

In certain embodiments of the catalyst materials as described herein, the catalyst material exhibits a test conversion of CO that is more than about 60%, or more than about 62%, or more than about 65%, or more than about 67%, or more than about 70%, or more than about 72%, or more than about 75%, or more than about 78%, or even more than about 80%. The "test conversion", as used herein, refers to the conversion in a test reaction performed at 200 to 280° C. in a set of tubular reactors (i.d.=19 mm) with 10 mL whole particle loading, at 400 psi, dry gas space velocity (DGSV)=5000 h$^{-1}$, steam/gas=0.6.

The catalyst materials and methods of the disclosure are illustrated further by the following examples, which are not to be construed as limiting the disclosure in scope or spirit to the specific procedures and in them.

EXAMPLES

Example 1

Comparative

A sample including copper and stabilizer oxide (CuO/ZnO=34/66) was made by co-precipitation. 179 g of 15.2% copper (II) nitrate solution was mixed with 326 g of 16.3% zinc nitrate solution, then the mixture was diluted with deionized water to form 1 liter of solution. Then the mixed metal nitrate solution was precipitated with 20% $Na_2CO_3$ solution. The precipitate was washed then calcined to provide a mixed oxide material. The powder material was formed into tablets with 3% graphite as a lubricant (sample-1).

Example 2

Comparative

A sample including copper and stabilizer oxide components (CuO/ZnO/$Al_2O_3$=45/45/10) was made by co-precipitation. 238 g of 15.2% copper (II) nitrate solution was mixed with 222 g of 16.3% zinc nitrate solution and 133 g of 4 aluminum nitrate solution, then the mixture was diluted with deionized water to form 1 liter of solution. Then the mixed metal nitrate solution was precipitated with 20% $Na_2CO_3$ solution. The precipitate was washed then calcined to provide a mixed oxide material. The powder material was formed into tablets with 3% graphite as a lubricant (sample-2).

Example 3

Comparative

A sample with copper and multiple-valence components (CuO/$MnO_2$=50/50) was made by co-precipitation. 265 g of 15.2% copper (II) nitrate solution was mixed with 340 g of 9.3% manganese (IV) nitrate solution, then the mixture was diluted with deionized water to form 1 liter of solution. Then the mixed metal nitrate solution was precipitated with 20% $Na_2CO_3$ solution. The precipitate was washed then calcined to provide a mixed oxide material. The powder material was formed into tablets with 3% graphite as a lubricant (sample-3).

Example 4

A CuO/ZnO/$MnO_2$ composition (45/45/10) was made by co-precipitation. 238 g of 15.2% copper (II) nitrate solution was mixed with 222 g of 16.3% zinc nitrate solution and 68.5 g of 9.3% manganese (IV) nitrate solution, then the mixture was diluted with deionized water to form 1 liter of solution. Then the mixed metal nitrate solution was precipitated with 20% $Na_2CO_3$ solution. The precipitate was washed then calcined to provide a mixed oxide material. The powder material was formed into tablets with 3% graphite as a lubricant (sample-4).

Example 5

A CuO/ZnO/$CeO_2$ composition (47.5/47.5/5) was made by co-precipitation. 12.6 g Ce(NO$_3$)$_3$ salt was dissolved in deionized water followed by mixing with 267 g of 15.2% copper (II) nitrate solution and 238 g of 16.3% zinc nitrate solution. The mixed solution was diluted with deionized water to form 1 liter of solution. Then the mixed metal nitrate solution was precipitated with 20% $Na_2CO_3$ solution. The precipitate was washed then calcined to provide a mixed oxide material. The powder material was formed into tablets with 3% graphite as a lubricant (sample-5).

Example 6

A CuO/$Al_2O_3$/$MnO_2$ composition (50/49/1) was made by co-precipitation. 264 g of 15.2% copper(II) nitrate solution was mixed with 648 g of 4% aluminum nitrate solution and 7.4 g of 9.3% manganese (IV) nitrate solution, then the mixture was diluted with deionized water to form 1 liter of solution. Then the mixed metal nitrate solution was precipitated with 20% $Na_2CO_3$ solution. The precipitate was washed then calcined to provide a mixed oxide material. The powder material was formed into tablets with 3% graphite as a lubricant (sample-6).

Example 7

A CuO/$Al_2O_3$/$MnO_2$ composition (45/45/10) was made by co-precipitation. 240 g of 15.2% copper (II) nitrate solution was mixed with 596 g of 4 aluminum nitrate solution and 67.8 g of 9.3% manganese (IV) nitrate solution, then the mixture was diluted with deionized water to form 1 liter of solution. Then the mixed metal nitrate solution was precipitated with 20% $Na_2CO_3$ solution. The precipitate was washed then calcined to provide a mixed oxide material. The powder material was formed into tablets with 3% graphite as a lubricate (sample-7).

Example 8

A $CuO/Al_2O_3/MnO_2$ composition (50/30/20) was made by co-precipitation. 265 g of 15.2% copper (II) nitrate solution was mixed with 398 g of 4% aluminum nitrate solution and 135.5 g of 9.3% manganese (IV) nitrate solution, then the mixture was diluted with deionized water to form 1 liter of solution. Then the mixed metal nitrate solution was precipitated with 20% $Na_2CO_3$ solution. The precipitate was washed then calcined to provide a mixed oxide material. The powder material was formed into tablets with 3% graphite as a lubricate (sample-8).

Examples 9-11

In Examples 9-11, samples made in Examples 1-8 were tested in lab-scale olefin hydrogenation and CO shift reactions simultaneously at different reaction conditions in a set of tubular reactors (i.d.=19 mm) with 10 mL whole particle loading. All samples were reduced in-situ at 230° C. with 3% $H_2$ in $N_2$ gas before the hydrogenation/shift process. Table 1 provides dry gas compositions of two gases tested.

TABLE 1

| Component | Concentration, mole % | |
| --- | --- | --- |
| | Gas-1 | Gas-2 |
| CO + $H_2$ | 23.5 | 46.8 |
| $CO_2$ | 39 | 24 |
| $CH_4$ | 29 | 17.5 |
| $N_2$ | 6.4 | 6.5 |
| $C_2H_6$ | 1 | 2.5 |
| $C_2H_4$ | 0.1 | 0.3 |
| $C_3H_8$ | 0.5 | 1.2 |
| $C_3H_6$ | 0.5 | 1.2 |

Example 9

Kinetic performance of samples 1-8 was evaluated with Gas-1 at 204° C. and 275° C., at 400 psi, steam/gas=0.6, dry gas space velocity (DGSV)=5000 $h^{-1}$. The results are shown in Table 2 below.

TABLE 2

| | Conversion, % | | | | | |
| --- | --- | --- | --- | --- | --- | --- |
| | T = 204° C. | | | T = 275° C. | | |
| Sample | X % CO | X % $C_2H_4$ | X % $C_3H_6$ | X % CO | X % $C_2H_4$ | X % $C_3H_6$ |
| S-1 | 71.9 | 82.8 | 59.7 | 85.9 | 93.5 | 86.3 |
| S-2 | 76.5 | 83.7 | 60.5 | 86.3 | 94.9 | 89.7 |
| S-3 | 71.8 | 73.2 | 41.4 | 79.6 | 91.9 | 70.4 |
| S-4 | 85.2 | 89.3 | 68.8 | 91.0 | 98.3 | 95.0 |
| S-5 | 84.9 | 93.6 | 78.9 | 89.2 | 99.0 | 97.2 |
| S-6 | 87.1 | 90.5 | 62.7 | 92.6 | 98.5 | 96.9 |
| S-7 | 93.2 | 94.2 | 74.5 | 93.3 | 98.9 | 97.0 |
| S-8 | 93.9 | 96.8 | 79.0 | 93.1 | 99.2 | 96.7 |

The test results demonstrate that catalyst materials described herein are more active for both hydrogenating olefins and shifting CO than the copper-based catalysts commonly used for hydrogenation and shift reactions.

Example 10

Thermal stability of samples 1-8 was evaluated with a high temperature cycling protocol, 72 hours at 204° C.→32 hours at 275° C.→32 hours at 350° C.→48 hours at 204° C., Gas-1 was used as gas feed, at 400 psi, steam/gas=0.6, DGSV=5000 $h^{-1}$. The results are shown in Table 3 below.

TABLE 3

| | Conversion at 204° C., % | | | | | |
| --- | --- | --- | --- | --- | --- | --- |
| | Before thermal treatment | | | After thermal treatment | | |
| Sample | X % CO | X % $C_2H_4$ | X % $C_3H_6$ | X % CO | X % $C_2H_4$ | X % $C_3H_6$ |
| S-1 | 71.9 | 82.8 | 59.7 | 71.0 | 81.2 | 59.2 |
| S-3 | 71.8 | 73.2 | 41.4 | 57.4 | 54.1 | 22.4 |
| S-4 | 85.2 | 89.3 | 68.8 | 86.1 | 89.4 | 71.8 |
| S-6 | 87.1 | 90.5 | 62.7 | 86.2 | 90.5 | 62.7 |
| S-7 | 93.2 | 94.2 | 74.5 | 93.4 | 94.2 | 71.1 |
| S-8 | 93.9 | 96.8 | 79.0 | 91.8 | 92.8 | 68.9 |

The test results demonstrate that catalyst materials described herein are more active and more stable for both hydrogenating olefins and shifting CO than the copper based catalysts commonly used for hydrogenation and shift reactions.

Example 11

Effect of conditions on catalyst performance was evaluated for sample-3 and sample-7. Catalytic performance was evaluated with Gas-2 at 275° C., at 400 psi, steam/gas=0.6. The results are shown in Table 4 below.

TABLE 4

| | Conversion, % | | |
| --- | --- | --- | --- |
| Sample | X % CO | X % $C_2H_4$ | X % $C_3H_6$ |
| S-3 | 67.9 | 86.5 | 71.2 |
| S-7 | 90.8 | 99.4 | 97.6 |

The test results demonstrate that catalyst materials described herein have a superior performance over sample-3 (which contains copper and stabilizer oxide components only) at higher concentration of CO+$H_2$ and olefins in the feed.

Example 12

Figure 1:
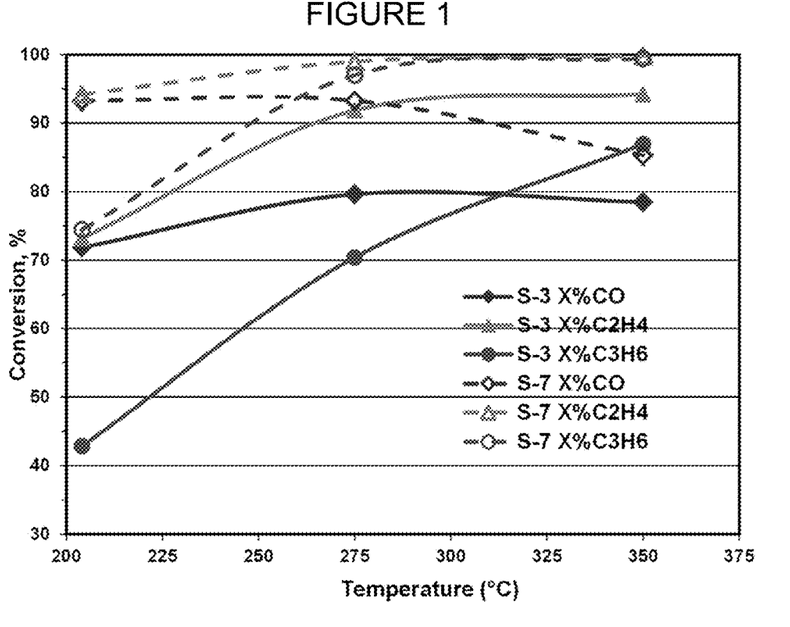
FIG. 1 is a graph depicting the results of an investigation of the effect of thermal treatment on catalytic activity of catalysts according to certain embodiments of the disclosure.

The activities of the catalyst materials described above at various reaction temperatures are shown in FIG. 1. The reaction was tested with Gas-1 as gas feed, steam/gas=0.6, DGSV=5000 h$^{-1}$. Sample 7 had much higher activities for hydrogenating olefins and shifting CO than Sample 3 in all ranges of temperature tested, and with increasing reaction temperature, catalyst activities increased as well. Conversions of olefins and CO approached equilibrium over Sample 7 catalyst at temperature over 275° C. For sample 3, the conversions of olefins and CO did not reach equilibrium by 350° C. temperature.

Example 13

Figure 2:
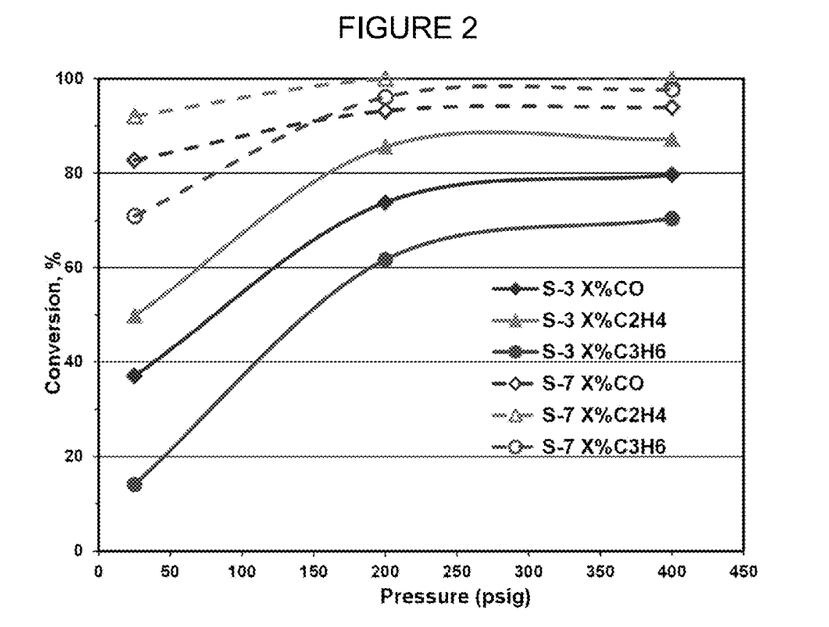
FIG. 2 is a graph depicting the results of an investigation of the effect of pressure on catalytic activity of catalysts according to certain embodiments of the disclosure.

The activities of the catalyst materials described above at various reaction pressures are shown in FIG. 2. The reaction was tested with Gas-1 as gas feed, at 275° C., steam/gas=0.6. Sample 7 had much higher activities for hydrogenating olefins and shifting CO than Sample 3 in all range of pressures tested, and with increasing reaction pressure, catalyst activities increased as well. Conversions of olefins and CO approached equilibrium over Sample 7 catalyst at 400 psig pressure, while they were far away from equilibrium over Sample 3 catalyst.

Example 14

Figure 3:
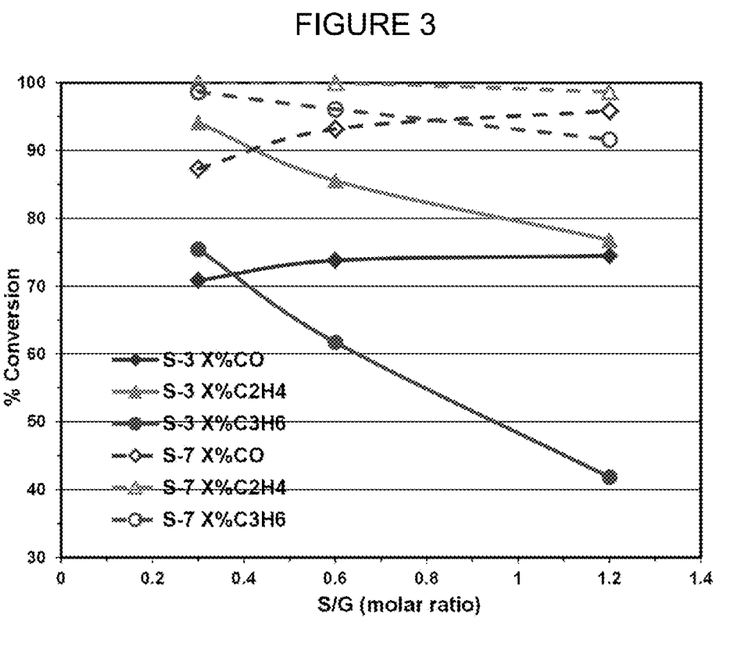
FIG. 3 is a graph depicting the results of an investigation of the effect of steam to gas molar ratio (S/G) in the feedstock on catalytic activity of catalysts according to certain embodiments of the disclosure.

The activities of the catalyst materials described above at various steam to gas molar ratio (S/G) in the feedstock are shown in FIG. 3. The reaction was tested with Gas-1 as gas feed, at 275° C., 200 psig. Sample 7 had much higher activities for hydrogenating olefins and shifting CO than Sample 3 in all range of steam to gas ratios tested. With increasing steam to gas ratios, catalyst activities for CO conversion increased while hydrogenation activity was suppressed. However, conversion of olefins decreased less over Sample 7 than over Sample 3.

Example 15

Figure 4:
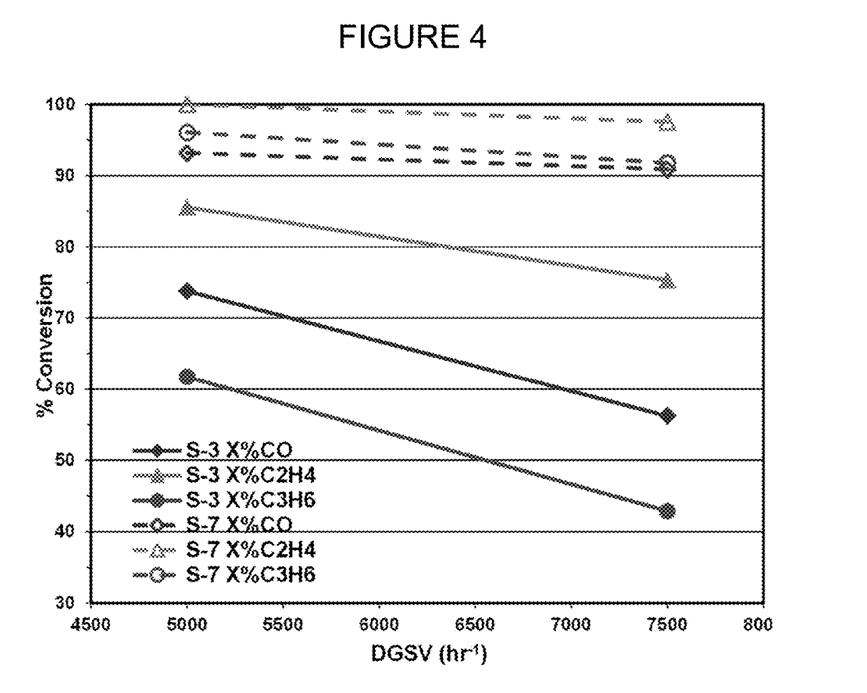
FIG. 4 is a graph depicting the results of an investigation of the effect of dry gas space velocity (DGSV) on catalytic activity of catalysts according to certain embodiments of the disclosure.

The activities of the catalyst materials described above at various dry gas space velocities (DGSVs) are shown in FIG. 4. The reaction was tested with Gas-1 as gas feed, at 275° C., steam/gas=0.6. Sample 7 had much higher activities for hydrogenating olefins and shifting CO than Sample 3 in all range of DGSVs tested. With increasing DGSVs, catalyst activities decreased due to shortened contact time of the feed with the catalyst. The conversion of both olefins and CO, however, was affected less over Sample 7 than over Sample 3.

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

We claim:
1. A catalyst material comprising:
(a) copper, present in the range of about 20 weight % to about 80 weight % based on the total weight of the catalyst material, calculated as CuO;
(b) one or more stabilizer oxides, each stabilizer oxide being selected from the group consisting of group consisting of zinc oxide, aluminum oxide, zirconium oxide, titanium oxide, silicon dioxide, zinc aluminate, magnesium aluminate, zinc aluminate and silica aluminate, calcium aluminate, clays and zeolites and mixtures thereof, each stabilizer oxide being stable under reducing conditions, the one or more stabilizer oxides being present in a total amount in the range of about 20 weight % to about 70 weight % based on the total weight of the catalyst material, calculated as the most stable oxide for each metal; and
(c) one or more multiple-valence metals, each multiple valence metal being selected from manganese, cerium, chromium, vanadium, iron, cobalt, lanthanum, nickel, molybdenum and tungsten, each multiple-valence metal being present in a positive oxidation state, the one or more multiple-valence metals are present in the range of about 0.1 weight % to about 40 weight % based on the total weight of the catalyst material, calculated as the most stable oxide for each metal.

2. The catalyst material of claim 1, wherein the copper is present as metallic copper.

3. The catalyst material of claim 1, wherein the copper is present in the form of copper oxide.

4. The catalyst material of claim 1, wherein the copper is present in the range of about 35 weight % to about 55 weight % based on the total weight of the catalyst material, calculated as CuO.

5. The catalyst material of claim 1, wherein the one or more stabilizer oxides is zinc oxide, aluminum oxide, zinc aluminate or a mixture thereof.

6. The catalyst material of claim 1, wherein the one or more stabilizer oxides are present in the range of about 30 weight % to about 60 weight % based on the total weight of the catalyst material, calculated as the most stable oxide for each metal.

7. The catalyst material of claim 1, wherein the weight ratio of the copper to the one or more stabilizer oxides is in the range of about 3:1 to about 1:2.

8. The catalyst material of claim 7, wherein the weight ratio of the copper to the one or more multiple-valence metals is in the range of about 5:0.01 to about 5:3, both calculated as oxide.

9. The catalyst material of claim 1, wherein the weight ratio of the copper to the one or more stabilizer oxides is in the range of about 1.5:1 to about 1:1.2.

10. The catalyst material of claim 1, wherein the one or more multiple-valence metals are selected from group consisting of manganese, cerium, vanadium, iron, cobalt, nickel, molybdenum and tungsten.

11. The catalyst material of claim 1, wherein the one or more multiple-valence metals are selected from group consisting of manganese and cerium.

12. The catalyst material of claim 1, wherein the one or more multiple-valence metals are present in the form of one or more oxides.

13. The catalyst material of claim 1, wherein the one or more multiple-valence metals are present in the range of about 0.5 weight % to about 20 weight % based on the total weight of the catalyst material, calculated as the most stable oxide for each metal.

14. The catalyst material of claim 1, wherein the weight ratio of the copper to the one or more multiple-valence metals is in the range of about 5:0.01 to about 5:3, both calculated as oxide.

15. The catalyst material of claim 1, wherein the one or more stabilizer oxides is selected from zinc oxide and aluminum oxide; and the one or more multiple-valence metals are selected from manganese or cerium.

16. The catalyst material of claim 15, wherein the copper present in the range of about 40 weight % to about 55 weight %, calculated as CuO; the stabilizer oxide is present in an amount of about 30 weight % to about 50 weight %, calculated as the most stable oxide for each metal; and the multiple-valence metal is present in an amount of about 1 weight % to about 25 weight %, calculated as the most stable oxide for each metal.

17. The catalyst material of claim 1, including less than about 20%, of components other than the copper, the stabilizer oxide and the multiple-valence metal.

18. The catalyst material of claim 1, containing less than 1% of components other than the copper, the stabilizer oxide(s) and the one or more multiple-valence metal(s).

19. The catalyst material of claim 1, wherein the multiple-valence metal is cerium.

20. The catalyst material of claim 1, disposed in contact with an off-gas stream of a Fischer-Tropsch process, the off-gas stream comprising an olefin and carbon monoxide.

21. The catalyst material of claim 1, wherein the one or more multiple-valence metals are selected from group consisting of cerium, vanadium, iron, cobalt, nickel, molybdenum and tungsten.

22. A method for converting carbon monoxide to carbon dioxide, the method comprising reacting carbon monoxide with water in contact with a catalyst material of claim 1.

23. A method for converting olefins to hydrocarbons, the method comprising reacting an olefin with hydrogen in contact with a catalyst material of claim 1.

24. A method for simultaneously converting carbon monoxide to carbon dioxide and olefins to hydrocarbons, the method comprising reacting carbon monoxide with water, and one or more olefins with hydrogen in contact with a catalyst material of claim 1.

* * * * *